United States Patent [19]

Nakai et al.

[11] Patent Number: 5,705,678
[45] Date of Patent: Jan. 6, 1998

[54] OXOTITANIUM COMPLEX, ASYMMETRIC HYDROGENATION CATALYST COMPRISING THE COMPLEX, AND PROCESS FOR PRODUCING β-HYDROXY KETONE OR α-HYDROXY CARBOXYLIC ACID ESTER USING THE COMPLEX

[75] Inventors: Takeshi Nakai, Kanagawa; Dai Kitamoto, Ibaraki; Noboru Sayo, Kanagawa, all of Japan

[73] Assignee: Takasago International Corporation, Tokyo, Japan

[21] Appl. No.: 775,192

[22] Filed: Dec. 30, 1996

Related U.S. Application Data

[62] Division of Ser. No. 401,800, Mar. 10, 1995, Pat. No. 5,616,751.

[30] Foreign Application Priority Data

Mar. 11, 1994 [JP] Japan ................................. 6-67607

[51] Int. Cl.⁶ .............................................. C07C 69/73
[52] U.S. Cl. ............................................... 560/183
[58] Field of Search ................................. 560/183

[56] References Cited

U.S. PATENT DOCUMENTS 3,134,737  5/1964  Kay .
5,344,945  9/1994  Verkade .

FOREIGN PATENT DOCUMENTS 219284  4/1987  European Pat. Off. .
241235  10/1987  European Pat. Off. .

OTHER PUBLICATIONS

Journal of the Chemical Society, Chm. Comm. No.7, Apr. 7, 1994, pp. 833–834, XP002003784, M. Terana et al. "Binaphthol–Derived Titanium Mu–Oxo Complex ... Reaction With Glycolate".

Journal of the American Chemical Society, vol. 117, No. 11, Feb. 22, 1995, pp. 3008–3021, XP002003785, A. Van Der Linden et al. "Polymerization of α–Olefins and Butadiene and Catalytic ... Zirconium Species".

*Primary Examiner*—Paul J. Killos
*Attorney, Agent, or Firm*—Sughrue, Mion, Zinn, Macpeak & Seas, PLLC

[57] ABSTRACT

A novel oxotitanium complex represented by general formula (I) is disclosed:

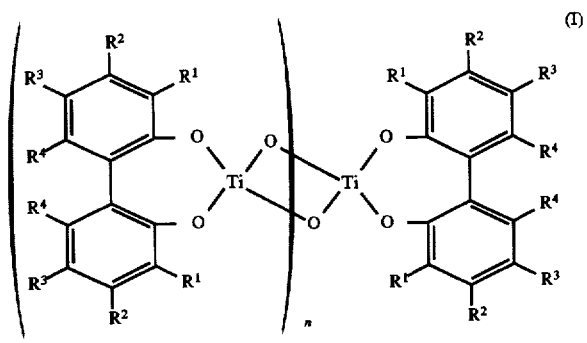

wherein $R^1$ and $R^2$ may be the same or different and each represents a hydrogen atom, a lower alkyl group, a lower alkoxy group, a halogen atom, a phenyl group, a substituted phenyl group, a trialkylsilyl group, a monoalkyldiphenylsilyl group, a dialkylmonophenylsilyl group, a triphenylsilyl group, a substituted triphenylsilyl group, or a lower alkoxycarbonyl group, provided that $R^1$ and $R^2$ may be bonded to each other to form a hydrocarbon ring or a substituted hydrocarbon ring in cooperation with the carbon atoms to which $R^1$ and $R^2$ are bonded; $R^3$ and $R^4$ may be the same or different and each represents a hydrogen atom, a lower alkyl group, a lower alkoxy group, a benzoyl group, a benzenesulfonyl group, or a halogen atom, provided that $R^3$ and $R^4$ may be bonded to each other to form a hydrocarbon ring or a substituted hydrocarbon ring in cooperation with the carbon atoms to which $R^3$ and $R^4$ are bonded; and n is 1 or 2. The novel oxotitanium complex is useful as an asymmetric reaction catalyst. A process for producing a β-hydroxy ketone or an α-hydroxy carboxylic acid ester in the presence of the novel oxotitanium complex is also disclosed.

1 Claim, No Drawings

OXOTITANIUM COMPLEX, ASYMMETRIC HYDROGENATION CATALYST COMPRISING THE COMPLEX, AND PROCESS FOR PRODUCING β-HYDROXY KETONE OR α-HYDROXY CARBOXYLIC ACID ESTER USING THE COMPLEX

This is a divisional of application Ser. No. 08/401,800 filed Mar. 10, 1995 U.S. Pat. No. 5,616,751.

FIELD OF THE INVENTION

The present invention relates to a novel oxotitanium complex represented by general formula (I), particularly to a novel oxotitanium complex useful as an asymmetric reaction catalyst. The present invention also relates to a process for producing a β-hydroxy ketone or an α-hydroxy carboxylic acid ester in the presence of the complex.

BACKGROUND OF THE INVENTION

Utilization of a complex comprising a titanium atom and organic ligands as a catalyst for asymmetric reactions has been widely known. Also known widely is the selection of an optically active compound, in particular an axially asymmetric hydroxylated compound, as an organic ligand of such complex.

It has been reported to select binaphthol as such hydroxylated compound and to utilize a titanium complex of this compound, i.e., a binaphthol-dichlorotitanium complex, as a catalyst for asymmetric synthesis (Mikami et al., *J. Am. Chem. Soc.*, 1989, 111, 1940).

Although this complex is an excellent asymmetric catalyst, it still has problems that the stability thereof is slightly insufficient and the preparation thereof is somewhat troublesome.

In contrast, a binaphthol-diisopropoxytitanium complex can be prepared extremely easily, but has low catalytic activity. Use of the binaphthol-diisopropoxytitanium complex as an asymmetric catalyst is therefore impractical.

On the other hand, a technique has been reported in which a complex obtained by causing binaphthol to coordinate to a hydrolyzate of titanium isopropoxide represented by the chemical formula

(i—Pro—O)$_2$Ti=O (wherein i-Pro represents an isopropyl group) is used as an asymmetric catalyst (Mukaiyama et al., *Chem. Lett.*, 1990, 1015).

The above asymmetric catalyst not only is insufficient in suitability for asymmetric reactions and in catalytic activity, but also has problems, for example, that the oxotitanium complex produced as an intermediate for the above complex catalyst is unstable and that the ligand exchange reaction tends not to proceed smoothly.

SUMMARY OF THE INVENTION

Accordingly, an object of the present invention is to overcome the problems of conventionally known asymmetric catalysts containing titanium, that is, to provide a titanium-containing complex which not only has excellent suitability for asymmetric reactions but is highly stable.

Another object of the present invention is to provide a process for efficiently producing the titanium-containing complex.

Still another object of the present invention is to provide a process in which the titanium-containing complex is used to produce either an α-hydroxy carboxylic acid ester or a β-hydroxy ketone which each has excellent optical activity.

As a result of intensive investigations made by the present inventors, they have found that a compound obtained by hydrolyzing a binaphthol-diisopropoxytitanium complex is extremely highly stable and also has excellent suitability for asymmetric reactions. Further investigations were made based on this finding, and the present invention has finally been achieved.

The present invention provides an oxotitanium complex represented by general formula (I):

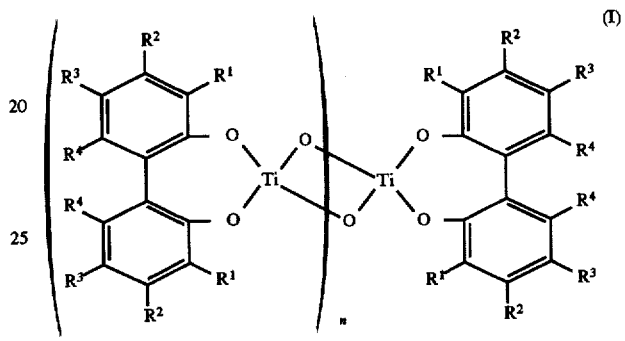

wherein $R^1$ and $R^2$ may be the same or different and each represents a hydrogen atom, a lower alkyl group, a lower alkoxy group, a halogen atom, a phenyl group, a substituted phenyl group, a trialkylsilyl group, a monoalkyldiphenylsilyl group, a dialkylmonophenylsilyl group, a triphenylsilyl group, a substituted triphenylsilyl group, or a lower alkoxycarbonyl group, provided that $R^1$ and $R^2$ may be bonded to each other to form a hydrocarbon ring or a substituted hydrocarbon ring in cooperation with the carbon atoms to which $R^1$ and $R^2$ are bonded; $R^3$ and $R^4$ may be the same or different and each represents a hydrogen atom, a lower alkyl group, a lower alkoxy group, a benzoyl group, a benzenesulfonyl group, or a halogen atom, provided that $R^3$ and $R^4$ may be bonded to each other to form a hydrocarbon ring or a substituted hydrocarbon ring in cooperation with the carbon atoms to which $R^3$ and $R^4$ are bonded; and n is 1 or 2.

The present invention also provides a process for producing an oxotitanium complex represented by general formula (I):

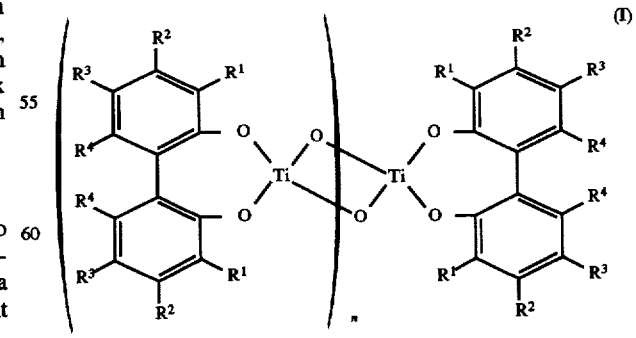

wherein $R^1$, $R^2$, $R^3$, and $R^4$ have the same meanings as defined above, which comprises hydrolyzing a compound represented by general formula (II):

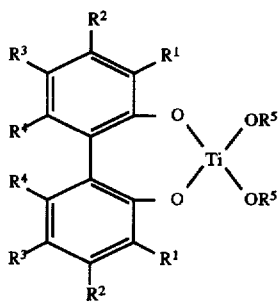
(II)

wherein $R^1$, $R^2$, $R^3$, and $R^4$ have the same meanings as defined above and $R^5$ represents methyl, ethyl, propyl, isopropyl, butyl, isobutyl, t-butyl, phenyl, o-tolyl, m-tolyl, p-tolyl, 3,5-xylyl, o-methoxyphenyl, m-methoxyphenyl, p-methoxyphenyl, o-chlorophenyl, m-chlorophenyl or p-chlorophenyl.

The present invention further provides a process for producing an α-hydroxy carboxylic acid ester represented by general formula (V):

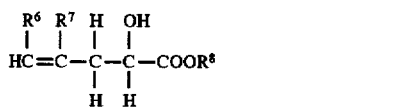
(V)

wherein $R^6$ represents a hydrogen atom or a lower alkyl group and $R^7$ represents a lower alkyl group, a phenyl group, or a cycloalkyl group, provided that $R^6$ and $R^7$ may be bonded to each other to form a hydrocarbon ring in cooperation with the carbon atoms to which $R^6$ and $R^7$ are bonded, and $R^8$ represents a lower alkyl group, which comprises reacting an olefin compound represented by general formula (III):

(III)

wherein $R^6$ and $R^7$ have the same meanings as defined above, with a glyoxylate compound represented by general formula (IV):

(IV)

wherein $R^8$ has the same meaning as defined above, in the presence of the oxotitanium complex represented by general formula (I) described above.

The present invention still further provides a process for producing a β-hydroxy ketone represented by general formula (VIII):

(VIII)

wherein $R^9$ and $R^{10}$ may be the same or different and each represents a hydrogen atom or a lower alkyl group, $R^{11}$ represents a lower alkyl group, a lower alkoxy group, a phenyl group, a phenoxy group, or a lower alkylthio group, and $R^{15}$ represents a lower alkyl group, a lower alkoxymethyl group, a phenyl group, a substituted phenyl group, a benzyloxymethyl group, or a lower alkoxycarbonyl group, which comprises reacting a silyl enol ether compound represented by general formula (VI):

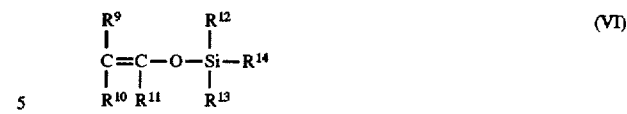
(VI)

wherein $R^9$, $R^{10}$, and $R^{11}$ have the same meanings as defined above, and $R^{12}$, $R^{13}$, and $R^{14}$ may be the same or different and each represents a lower alkyl group or a phenyl group, with an aldehyde compound represented by general formula (VII):

(VII)

wherein $R^{15}$ has the same meaning as defined above, in the presence of the oxotitanium complex represented by general formula (I) described above.

DETAILED DESCRIPTION OF THE INVENTION

The oxotitanium complex of the present invention, which is represented by general formula (I) described above, specifically includes the dimers and trimers represented by the following general formulae.

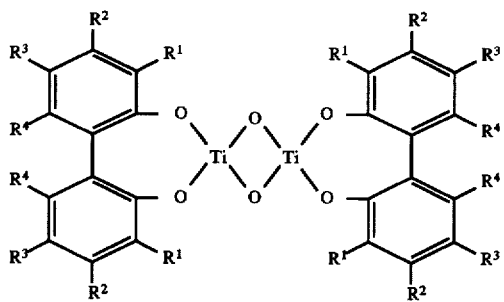

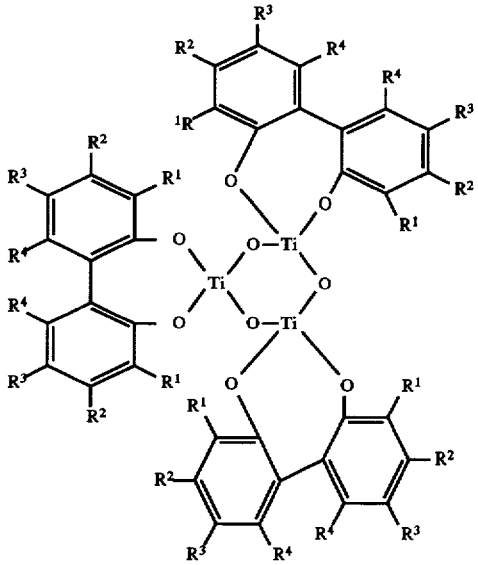

The oxotitanium complex of the present invention may be a mixture of such dimer and such trimer.

Examples of $R^1$ in the above-described general formula (I) include hydrogen atom; lower alkyl groups such as methyl, ethyl, propyl, and butyl; lower alkoxy groups; halogen atoms; phenyl group and phenyl groups each substituted with, e.g., a halogen atom, a lower alkyl group, or a hydroxyl group; trialkylsilyl groups, monoalkyldiphenylsilyl groups, and dialkylmonophenylsilyl groups (wherein the alkyls are lower alkyl groups); triphenylsilyl group and triphenylsilyl groups each substituted with one or more lower alkyl groups (e.g., ditolylphenylsilyl group or tritolylsilyl group); and lower alkoxycarbonyl groups (hereinafter "a lower alkoxy group" means methoxy, ethoxy, propoxy, butoxy, or the like).

Examples of $R^2$ are the same as those of $R^1$. $R^1$ and $R^2$ may be bonded to each other to form a hydrocarbon ring in cooperation with the carbon atoms to which $R^1$ and $R^2$ are bonded. This hydrocarbon ring may be substituted with, e.g., a lower alkyl group, a lower alkoxy group, a nitryl group, a hydroxyl group, or a halogen atom.

Examples of $R^3$ and $R^4$ include hydrogen atom, lower alkyl groups, lower alkoxy groups, benzoyl group, benzenesulfonyl group, and halogen atoms. $R^3$ and $R^4$ may be bonded to each other to form, in cooperation with the carbon atoms to which $R^3$ and $R^4$ are bonded, either a hydrocarbon ring or a hydrocarbon ring having a substituent such as, e.g., a lower alkyl group, a lower alkoxy group, a nitryl group, a halogen atom, or a hydroxyl group.

In the present invention, the term "lower alkyl group" means a linear or branched hydrocarbon group having 1 to 5 carbon atoms. The term "hydrocarbon ring" means a 5- to 7-membered saturated or unsaturated hydrocarbon ring.

Preferred examples of the oxotitanium complex of the present invention include the following:

Group 1

Oxotitanium complexes represented by general formula (I) in which $R^1$ is a group selected from a methyl group, a phenyl group, a substituted phenyl group, a triphenylsilyl group, a substituted triphenylsilyl group, and a lower alkoxycarbonyl group, $R^2$ is a hydrogen atom, and $R^3$ and $R^4$ are bonded to each other to form, in cooperation with the carbon atoms to which $R^3$ and $R^4$ are bonded, either a hydrocarbon ring or a hydrocarbon ring having a substituent selected from a halogen atom, a benzoyl group, and a benzenesulfonyl group;

Group 2

Oxotitanium complexes represented by general formula (I) in which $R^1$ is a hydrogen atom, $R^2$ is a hydrogen atom, and $R^3$ and $R^4$ are bonded to each other to form, in cooperation with the carbon atoms to which $R^3$ and $R^4$ are bonded, either a hydrocarbon ring or a hydrocarbon ring having a substituent selected from a halogen atom, a benzoyl group, and a benzenesulfonyl group;

Group 3

Oxotitanium complexes represented by general formula (I) in which $R^1$ and $R^2$ are bonded to each other to form, in cooperation with the carbon atoms to which $R^1$ and $R^2$ are bonded, either a hydrocarbon ring or a hydrocarbon ring having a substituent selected from a halogen atom, a benzoyl group, and a benzenesulfonyl group, and $R^3$ and $R^4$ are bonded to each other to form, in cooperation with the carbon atoms to which $R^3$ and $R^4$ are bonded, either a hydrocarbon ring or a hydrocarbon ring having a substituent selected from a halogen atom, a benzoyl group, and a benzenesulfonyl group; and Group 4

Oxotitanium complexes represented by general formula (I) in which $R^1$ is a hydrogen atom, $R^2$ and $R^3$ each is a hydrogen atom, a halogen atom, or a group selected from a lower alkyl group and a lower alkoxy group, and $R^4$ is a methyl group.

Especially preferred examples of the oxotitanium complex of the present invention are oxotitanium complexes represented by general formula (I) which have either a hydrocarbon ring or a hydrocarbon ring having a substituent such as those enumerated above, in particular which have either a binaphthol ring or a binaphthol ring having a substituent such as those enumerated above.

A process for producing the oxotitanium complex of the present invention is explained below.

First, a compound represented by general formula (II) is prepared. This compound is then hydrolyzed to produce the oxotitanium complex.

The compound represented by general formula (II) can be prepared by known methods. It is, however, preferred to mix a titanium tetraalkoxide with an axially disymmetric diol in an organic solvent to synthesize the compound represented by general formula (II). An example of this synthesis method is proposed by T. Wang et al. (*Synthesis*, 1989, 291).

This compound represented by general formula (II) is added to an organic solvent. The organic solvent preferably contains a small amount of water. Heating this mixture with stirring yields the desired complex (so-called in-situ method).

Also usable are a method in which the reaction mixture resulting from the heating with stirring is refluxed to obtain the complex; and a method in which the reaction mixture resulting from the heating with stirring is refluxed and the solvent is then removed by an azeotropic treatment to obtain the complex (so-called isolation method). Such isolation methods are desirable in that the complex thus produced has especially high reactivity. Preferred of such isolation methods are those involving an azeotropic treatment, because the complex prepared via an azeotropic treatment not only is highly reactive but also is effective in efficiently producing an optically active compound.

The organic solvent used for the preparation of this complex may be one different from the organic solvent used for the preparation of the compound represented by the above-described general formula (II). It is however preferred to use the same organic solvent in the two syntheses.

Use of the same solvent enables a process in which a titanium tetraalkoxide is reacted with an axially disymmetric diol in the organic solvent to synthesize the compound represented by general formula (II) and this compound is then hydrolyzed, without being isolated and purified, by mixing water with the resulting reaction mixture with heating. Namely, the oxotitanium complex can be prepared from the titanium tetraalkoxide and the axially disymmetric diol by one step without isolation of the compound of general formula (II).

The organic solvent is not particularly limited as long as it readily reacts with neither the titanium tetraalkoxide nor the axially disymmetric diol nor the compound represented by general formula (II). However, preferred examples thereof include aromatic hydrocarbons such as benzene, toluene, and xylene, halogenated hydrocarbons such as methylene chloride, chloroform, and carbon tetrachloride, and aprotic solvents such as tetrahydrofuran, diethyl ether, and dimethoxyethane. Particularly preferred of these are aromatic hydrocarbons, especially toluene.

Although the conditions for the heating with stirring are not particularly limited as long as the desired compound represented by general formula (I) can be produced, preferred examples of the conditions are as follows.

When the water is added to the organic solvent, the amount of the water is preferably from 0.5 to 2.0 equivalents, more preferably from 0.8 to 1.5 equivalents, particularly preferably from 0.9 to 1.2 equivalents, to the axially disymmetric diol. If the water amount is outside the above range, the efficiency of complex formation is lowered.

Any reaction temperature in the range of from room temperature to the reflux temperature for the organic solvent may be used. However, the reaction is preferably carried out at the reflux temperature for the organic solvent used.

The reaction time varies depending on the kinds of the organic solvent, titanium tetraalkoxide, and axially disymmetric diol used. However, the reaction time is generally from 10 to 180 minutes, desirably from 15 to 100 minutes, preferably from 25 to 60 minutes.

After the reaction has been conducted for a predetermined period, the organic solvent, water, unreacted reactants, etc. are preferably removed from the reaction system by a known method, e.g., azeotropic distillation; this brings about more satisfactory results. The complex obtained after the reaction mixture is subjected to azeotropic distillation is excellent in suitability for asymmetric reactions, catalytic activity, etc.

Examples of the alkoxide in the titanium tetraalkoxide include methoxide, ethoxide, propoxide, and isopropoxide. Especially preferred of these is isopropoxide.

The axially disymmetric diol is defined as a compound having a skeleton comprising two aromatic rings directly bonded to each other. Examples thereof include biphenol, binaphthol, octahydrobinaphthol, and these compounds having any of the substituents enumerated hereinabove. Especially preferred of these are binaphthol and binaphthols having any of the above-enumerated substituents.

The (R) or the (S) isomer of the axially disymmetric diol may be selected, and the (R) or the (S) isomer of the oxotitanium complex is obtained accordingly. Either of these isomers may be selected and used according to the absolute configuration of the desired product.

The complex obtained by the above-described method may be purified further, and this higher-purity complex is used as a catalyst, in particular as an asymmetric catalyst, for producing, e.g., the compounds specified below. However, purification is not always necessary.

With the complex thus obtained, either an α-hydroxy carboxylic acid ester or a β-hydroxy ketone can be easily produced. These compounds have extremely high optical purity.

The process for producing the α-hydroxy carboxylic acid ester is explained first below.

The α-hydroxy carboxylic acid ester according to the present invention is represented by general formula (V):

$$\begin{array}{cccc} R^6 & R^7 & H & OH \\ | & | & | & | \\ HC=C-&C-&C-&COOR^8 \\ & & | & | \\ & & H & H \end{array} \quad (V)$$

wherein $R^6$ represents a hydrogen atom or a lower alkyl group and $R^7$ represents a lower alkyl group, a phenyl group, or a cycloalkyl group, provided that $R^6$ and $R^7$ may be bonded to each other to form a hydrocarbon ring in cooperation with the carbon atoms to which $R^6$ and $R^7$ are bonded, and $R^8$ represents a lower alkyl group.

This α-hydroxy carboxylic acid ester is obtained by reacting an olefin compound represented by general formula (III):

wherein $R^6$ and $R^7$ are the same as defined above, with a glyoxylate compound represented by general formula (IV):

wherein $R^8$ is the same as defined above.

Preferred examples of the compound represented by general formula (III) described above include 2-methyl-1-propene, 2-methyl-1-butene, 2-methyl-1-pentene, 2-methyl-1-hexene, 2,3-dimethyl-1-propene, 2,3-dimethyl-1-butene, 2,3,3-trimethyl-1-butene, 2-ethyl-1-propene, 2-ethyl-1-butene, α-methylstyrene, cyclopentylidene, cyclohexylidene, cycloheptylidene, α-pinene, and limonene.

Examples of the compound represented by general formula (IV), as the other starting compound, include methyl glyoxylate, ethyl glyoxylate, isopropyl glyoxylate, n-butyl glyoxylate, and t-butyl glyoxylate.

These compounds may be produced, for example, by the method proposed by T. R. Kelly et al. (*Synthesis*, 1972, 544–545).

In the process of the present invention for producing the compound represented by general formula (V), the compound represented by general formula (III) is reacted with an almost equimolar amount of the compound represented by general formula (IV) in an organic solvent solution of the oxotitanium complex described above.

Examples of the organic solvent used include aromatic hydrocarbons such as benzene, toluene, and xylene, halogenated hydrocarbons such as methylene chloride, chloroform, and carbon tetrachloride, and aprotic solvents such as tetrahydrofuran, diethyl ether, and dimethoxyethane. Particularly preferred of these are halogenated hydrocarbons, especially methylene chloride.

The process for producing the compound represented by general formula (V) is explained below in more detail, but the production conditions can vary depending on the kinds of the organic solvent, starting materials, and complex used and on other factors.

The concentrations of the compound represented by general formula (III) and the compound represented by general formula (IV) in the organic solvent each is preferably about from 0.1 to 5 mol/liter.

The oxotitanium complex as a catalyst may be used in an amount of about from 0.02 to 1 mol, preferably about from 0.05 to 0.5 mol, more preferably about from 0.07 to 0.1 mol, per mol of the starting compound represented by general formula (III). Such a catalyst amount is advantageous in that this yields a reaction product having a high optical purity.

The reaction is preferably conducted at a temperature of about from −60° to 0° C., especially about from −30° to −10° C., for about from 3 to 20 hours.

After completion of the reaction, an alkali, e.g., an aqueous solution of sodium hydrogen carbonate, is added to the reaction mixture, and this mixture is extracted with a solvent, e.g., diethyl ether or ethyl acetate. The extract is dried, and the solvent is then distilled off. Purifying the residue by column chromatography, e.g., silica gel column chromatography, gives the intended optically active α-hydroxy carboxylic acid ester in high yield.

Next, the process of the present invention for producing the hydroxy ketone is explained below.

The β-hydroxy ketone according to the present invention is represented by general formula (VIII):

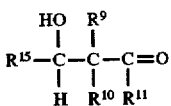

(VIII)

wherein $R^9$ and $R^{10}$ may be the same or different and each represents a hydrogen atom or a lower alkyl group, $R^{11}$ represents a lower alkyl group, a lower alkoxy group, a phenyl group, a phenoxy group, or a lower alkylthio group, and $R^{15}$ represents a lower alkyl group, a lower alkoxymethyl group, a phenyl group, a substituted phenyl group, a benzyloxymethyl group, or a lower alkoxycarbonyl group. The substituent for the substituted phenyl group includes a lower alkyl group, a lower alkoxy group, a hydroxy group, a halogen atom, a nitro group, an amino group, and a lower dialkylamino group.

This β-hydroxy ketone is produced by reacting a silyl enol ether compound represented by general formula (VI):

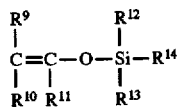

(VI)

wherein $R^9$, $R^{10}$, and $R^{11}$ are the same as defined above, and $R^{12}$, $R^{13}$, and $R^{14}$ may be the same or different and each represents a lower alkyl group or a phenyl group, with an aldehyde compound represented by general formula (VII):

$$R^{15}CHO \quad (VII)$$

wherein $R^{15}$ is the same as defined above, in the presence of the oxotitanium complex described above.

In the case where $R^{12}$, $R^{13}$, and $R^{14}$ in general formula (VI) described above each is methyl, examples of the compound represented by this general formula (VI) include methyl propionate-(E)-trimethylsilyl enol ether, methyl propionate-(Z)-trimethylsilyl enol ether, ethyl propionate-trimethylsilyl enol ether, isopropyl propionate-trimethylsilyl enol ether, phenyl propionate-trimethylsilyl enol ether, methyl acetate-trimethylsilyl enol ether, ethyl acetate-trimethylsilyl enol ether, phenyl acetate-trimethylsilyl enol ether, phenyl isobutyrate-trimethylsilyl enol ether, 3-pentanone-trimethylsilyl enol ether, 2-pentanone-trimethylsilyl enol ether, propiophenone-trimethylsilyl enol ether, S-t-butyl thiopropionate-trimethylsilyl enol ether, S-ethyl thiopropionate-trimethylsilyl enol ether, and S-ethyl thioacetate-trimethylsilyl enol ether.

Either the (E) isomer or the (Z) isomer of each of the above-enumerated compounds may be selected and used according to the absolute configuration of the desired product.

Each of these compounds represented by general formula (VI) may be synthesized from the corresponding ketone, ester, or thioester by the method described in *Silicon in Organic Synthesis*, (E. W. Colvin, Butterworths (London), 1981, pp. 198–287) or by the method proposed by N. Slougui et al. (*Synthesis*, p. 58, January, 1982).

For example, a preferred method for synthesizing the compound represented by general formula (VI) is as follows. A dialkylamine is dissolved in tetrahydrofuran, and this solution is cooled to about 0° C. An n-butyllithium solution in, e.g., tetrahydrofuran is then added thereto dropwise to obtain a lithium dialkylamide solution, which is then cooled to about −78° C. Thereto is added dropwise a compound selected from ketones, esters, thioesters, etc. About 30 minutes later, a silyl chloride derivative is added dropwise, and the reactants are allowed to sufficiently react at that temperature.

Examples of the compound represented by general formula (VII), as the other starting material, include acetaldehyde, ethanal, propanal, butanal, methoxymethylaldehyde, ethoxymethylaldehyde, propyloxymethylaldehyde, butyloxymethylaldehyde, benzyloxymethylaldehyde, methyl glyoxylate, ethyl glyoxylate, isopropyl glyoxylate, n-butyl glyoxylate, and t-butyl glyoxylate.

In a preferred method for synthesizing the compound represented by general formula (VIII), the compound represented by general formula (VI) is reacted with an almost equimolar amount of the compound represented by general formula (VII) in an organic solvent solution of the oxotitanium complex described above to produce a silyl-containing compound, which is then hydrolyzed.

Examples of the organic solvent used include aromatic hydrocarbons such as benzene, toluene, and xylene, halogenated hydrocarbons such as methylene chloride, chloroform, and carbon tetrachloride, and aprotic solvents such as tetrahydrofuran, diethyl ether, and dimethoxyethane. Particularly preferred of these are aromatic hydrocarbons, especially toluene.

The concentrations of the compound represented by general formula (VI) and the compound represented by general formula (VII) in the organic solvent each is preferably about from 0.1 to 5 mol/liter.

The oxotitanium complex as a catalyst may be used in an amount of about from 0.02 to 1 mol, desirably about from 0.05 to 0.5 mol, preferably about from 0.07 to 0.1 mol, per mol of the starting compound represented by general formula (VI). Such a catalyst amount is advantageous in that this yields a reaction product having a high optical purity.

The reaction is preferably conducted at a temperature of about from −50° to 0° C., especially about from −30° to −10° C., for about from 3 to 20 hours.

The thus-obtained compound containing a silyl group or a substituted silyl group is hydrolyzed in a known manner to prepare the corresponding β-hydroxy ketone.

A preferred hydrolysis method comprises dissolving the compound in an alcohol, e.g., methanol, ethanol, isopropanol, or n-butanol, adding a small amount of an acid, preferably an inorganic acid such as hydrochloric acid or sulfuric acid, and stirring the mixture at about 0° to 50° C. In another method, hydrogen chloride or hydrogen bromide is bubbled into an alcohol such as the above-enumerated ones or a small amount of hydrochloric acid, sulfuric acid, phosphoric acid, or the like is added to such an alcohol, and the compound containing a silyl group or a substituted silyl group is added to the thus-obtained alcohol solution, following which the mixture is stirred at about 0° to 50° C.

After completion of the reaction, an alkali, e.g., an aqueous solution of sodium hydrogen carbonate, is added to the reaction mixture, and this mixture is extracted with a solvent, e.g., diethyl ether or ethyl acetate. The extract is dried, and the solvent is then distilled off. Purifying the residue by column chromatography, e.g., silica gel column chromatography, gives the intended optically active β-hydroxy ketone in high yield.

The α-hydroxy carboxylic acid ester or β-hydroxy ketone obtained in high yield by the above-described process has a high optical purity and is extremely useful, e.g., as an intermediate for drugs and as a raw material for various functional materials.

The present invention will be explained below in more detail by reference to the following Examples, but the invention should not be construed as being limited thereto.

For the analyses in Examples, the following analytical instruments were used.

¹H Nuclear Magnetic Resonance Spectrometry (hereinafter abbreviated as "¹H-NMR"):
GEMINI Type 300 (300 MHz) (manufactured by Varian)
¹³C Nuclear Magnetic Resonance Spectrometry (hereinafter abbreviated as "¹³C-NMR"):
GEMINI Type 300 (75 MHz) (manufactured by Varian)
Polarimeter:
DIP-370 (manufactured by JEOL Ltd., Japan)

EXAMPLE 1

(R)(+)-Binaphthol in an amount of 286 mg (1 mmol) was added to 5 ml of toluene placed in a 30-ml two-necked reaction vessel the inside atmosphere of which had been replaced with nitrogen gas. The mixture was stirred at room temperature to obtain a suspension. Subsequently, 284 mg (1 mmol) of titanium tetraisopropoxide was added thereto, and the mixture was stirred for 15 minutes. Thereto was added 18 mg (1 mmol) of distilled water. This reaction mixture was stirred for 15 minutes, and then heated with refluxing for 20 minutes. The isopropanol present in the reaction mixture was removed by azeotropic distillation with toluene, and the solvent was then distilled off under reduced pressure. Thus, 357 mg of an oxotitanium complex was obtained. (yield: 98%)

¹H-NMR (300 MHz, CDCl₃) δ: 3.88 (s, 1H), 5.66 (d, J=8.6 Hz, 2H), 7.08–7.24 (m, 6H), 7.47 (dd, J=7.7, 7.2 Hz, 2H), 8.06 (d, J=8.3 Hz, 2H)

¹³C-NMR (75 MHz, CDCl₃) δ: 24.9, 117.3, 118. 3, 124.8, 126.7, 126.9, 129.9, 130.7, 133.2, 160.4

EXAMPLE 2

The same complex as prepared in Example 1 was dissolved in an amount of 18 mg (0.05 mmol) into 2 ml of methylene chloride placed in a 20-ml two-necked reaction vessel the inside atmosphere of which had been replaced with nitrogen gas. This solution was cooled to −30° C. Thereto were successively added 118 mg (1 mmol) of α-methylstyrene and a solution in 1 ml methylene chloride of 106 mg (1.2 mmol) of methyl glyoxylate. This mixture was stirred for about 3 hours.

After the reaction was terminated by adding 10 ml of saturated sodium hydrogen carbonate aqueous solution, the reaction mixture was filtered through Florisil and Celite. The aqueous layer was extracted with diethyl ether, and the organic layer obtained was washed with water and saturated aqueous common salt solution and then dried with anhydrous magnesium sulfate. The solvent was removed under reduced pressure, and the residue was purified by silica gel column chromatography (hexane/ethyl acetate=9/1 by volume) to obtain 190 mg of methyl 2-hydroxy-4-phenyl-4-pentenoate (yield: 92%).

This compound had an optical purity of 98% ee.

¹H-NMR (300 MHz, CDCl₃) δ: 2.74 (bs, 1H), 2.84 (dd, J=7.6, 14.4 Hz, 1H), 3.05 (dd, J=4.4, 14.4 Hz, 1H), 3.61 (s, 1H), 4.25–4.35 (m, 1H), 5.20 (bs, 1H), 5.40 (bs, 1H), 7.4 (m, 5H)

¹³C-NMR (75 MHz, CDCl₃) δ: 40.4, 52.2, 69.2, 116.4, 126.5, 127.8, 128.4, 140.3, 143.6, 174.8

EXAMPLE 3

The same procedure as in Example 2 was carried out, except that toluene was used in place of methylene chloride. Thus, 132 mg of methyl 2-hydroxy-4-phenyl-4-pentenoate was obtained (yield: 64%).

This compound had an optical purity of 97% ee.

REFERENCE EXAMPLE 1

Diisopropylamine in an amount of 2.42 g (24 mmol) was dissolved in 35 ml of tetrahydrofuran placed in a 100-ml two-necked reaction vessel the inside atmosphere of which had been replaced with nitrogen gas. This solution was cooled to 0° C., and 13.5 ml (22 mmol) of n-butyllithium (1.6N hexane solution) was added thereto dropwise. This mixture was stirred for 20 minutes. After the reaction mixture was cooled to −78° C., 2.61 g (26 mmol) of S-t-butyl thioacetate was gradually added thereto dropwise and the resulting mixture was stirred at −78° C. for 15 minutes. To this reaction mixture was gradually added dropwise 2.82 g (26 mmol) of chlorotrimethylsilane. This mixture was stirred first at −78° C. for 15 minutes and then at room temperature for 30 minutes.

After completion of the reaction, the reaction mixture was poured into a separatory funnel filled with hexane and ice-water to quickly conduct extraction. The organic layer was washed with saturated aqueous common salt solution, and the solvent was then removed under reduced pressure. The reaction product was purified by distillation (15 mmHg, 70° C.) to obtain 2.24 g of 1-S-t-butyl-1-(trimethylsilyl) oxyethene (yield: 50%).

EXAMPLE 4

The same complex as prepared in Example 1 was dissolved in an amount of 70 mg (0.2 mmol) into 2 ml of methylene chloride placed in a 30-ml two-necked reaction vessel the inside atmosphere of which had been replaced with nitrogen gas. This solution was cooled to −30° C.

Thereto were gradually added dropwise a solution in 2 ml of methylene chloride of 245 mg (1.2 mmol) of the compound obtained in Reference Example 1 and 106 mg (1 mmol) of benzaldehyde. This mixture was then stirred. About 15 hours later, 5 ml of a phosphoric acid buffer (pH 7) was added thereto to terminate the reaction. The reaction mixture was filtered through Florisil and Celite. The aqueous layer was extracted with diethyl ether, and the organic layer was washed with water and saturated aqueous common salt solution and then dried with anhydrous magnesium sulfate. The solvent was removed under reduced pressure, and the residue was purified by silica gel column chromatography (hexane/ethyl acetate=20/1 by volume) to obtain 217 mg of S-t-butyl 3-(trimethylsilyl)oxy-3-phenylthiopropionate (yield: 70%).

This compound was dissolved in 2 ml of methanol. After this solution was cooled to 0° C., several drops of 10% hydrochloric acid methanol solution were added and the resulting mixture was stirred for about 10 minutes.

The solvent was removed under reduced pressure, and the residue was dissolved in diethyl ether. This solution was washed with saturated aqueous common salt solution and subsequently dried with anhydrous magnesium sulfate. The solvent was then distilled off. The residue was purified by silica gel column chromatography (hexane/ethyl acetate= 20/1 by volume) to obtain 159 mg of S-t-butyl 3-oxy-3-phenylthiopropionate (yield: 95%).

This compound had an optical purity of 70% ee.

¹H-NMR (300 MHz, CDCl₃) δ: 1.47 (s, 9H), 2.82 (dd, J=3.9, 15.7 Hz, 1H), 2.73 (br, 1H), 2.89 (dd, J=8.6, 15.7 Hz, 1H), 5.15 (dd, J=3.9, 8.6 Hz, 1H), 7.2–7.4 (m, 5H)

¹³C-NMR (75 MHz, CDCl₃) δ: 29.6, 48.5, 52.6, 70.8, 125.7, 127.8, 128.6, 142.4, 200.2

According to the present invention, a novel complex is provided which is useful especially as a catalyst for asymmetric reactions. This complex, which can be synthesized by a relatively simple process, not only has good suitability for asymmetric reactions but also is highly stable and easily handleable. The complex of the present invention is useful especially as a catalyst for asymmetric glyoxylate-ene reactions or asymmetric aldol reactions for producing either intermediates for drugs or raw materials for various functional materials. In particular, the complex of the present invention is useful for efficiently synthesizing a highly optically active α-hydroxy carboxylic acid ester or β-hydroxy ketone.

While the invention has been described in detail and with reference to specific embodiments thereof, it will be apparent to one skilled in the art that various changes and modifications can be made therein without departing from the spirit and scope thereof.

What is claimed is:

1. A process for producing an α-hydroxy carboxylic acid ester represented by general formula (V):

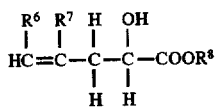

wherein $R^6$ represents a hydrogen atom or a lower alkyl group and $R^7$ represents a lower alkyl group, a phenyl group, or a cycloalkyl group, provided that $R^6$ and $R^7$ may be bonded to each other to form a hydrocarbon ring in cooperation with the carbon atoms to which $R^6$ and $R^7$ are bonded, and $R^8$ represents a lower alkyl group, or for producing a β-hydroxy ketone represented by general formula (VIII):

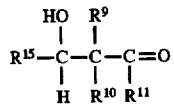

wherein $R^9$ and $R^{10}$ may be the same or different and each represents a hydrogen atom or a lower alkyl group, $R^{11}$ represents a lower alkyl group, a lower alkoxy group, a phenyl group, a phenoxy group, or a lower alkylthio group, and $R^{15}$ represents a lower alkyl group, a lower alkoxymethyl group, a phenyl group, a substituted phenyl group, a benzyloxymethyl group, or a lower alkoxycarbonyl group, which process comprises (A) reacting an olefin compound represented by general formula (III):

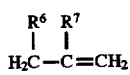

wherein $R^6$ and $R^7$ have the same meanings as defined above, with a glyoxylate compound represented by general formula (IV):

wherein $R^8$ has the same meaning as defined above, in the presence of an oxotitanium complex to thereby produce the α-hydroxy carboxylic acid ester, or (B) reacting a silyl enol ether compound represented by general formula (VI):

wherein $R^9$, $R^{10}$, and $R^{11}$ have the same meanings as defined above, and $R^{12}$, $R^{13}$, and $R^{14}$ may be the same or different and each represents a lower alkyl group or a phenyl group, with an aldehyde compound represented by general formula (VII):

wherein $R^{15}$ has the same meaning as defined above, in the presence of an oxotitanium complex to thereby produce the β-hydroxy ketone, wherein said oxotitanium complex is represented by general formula (I):

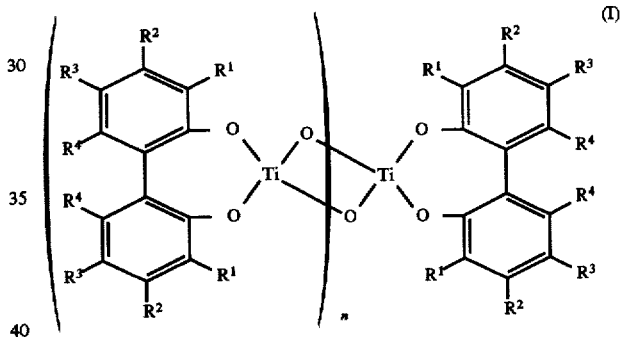

wherein $R^1$ and $R^2$ may be the same or different and each represents a hydrogen atom, a lower alkyl group, a lower alkoxy group, a halogen atom, a phenyl group, a substituted phenyl group, a trialkylsilyl group, a monoalkyldiphenylsilyl group, a dialkylmonophenylsilyl group, a triphenylsilyl group, a substituted triphenylsilyl group, or a lower alkoxycarbonyl group, provided that $R^1$ and $R^2$ may be bonded to each other to form a hydrocarbon ring or a substituted hydrocarbon ring in cooperation with the carbon atoms to which $R^1$ and $R^2$ are bonded; $R^3$ and $R^4$ may be the same or different and each represents a hydrogen atom, a lower alkyl group, a lower alkoxy group, a benzoyl group, a benzenesulfonyl group, or a halogen atom, provided that $R^3$ and $R^4$ may be bonded to each other to form a hydrocarbon ring or a substituted hydrocarbon ring in cooperation with the carbon atoms to which $R^3$ and $R^4$ are bonded; and n is 1 or 2.

* * * * *